Figure 1:
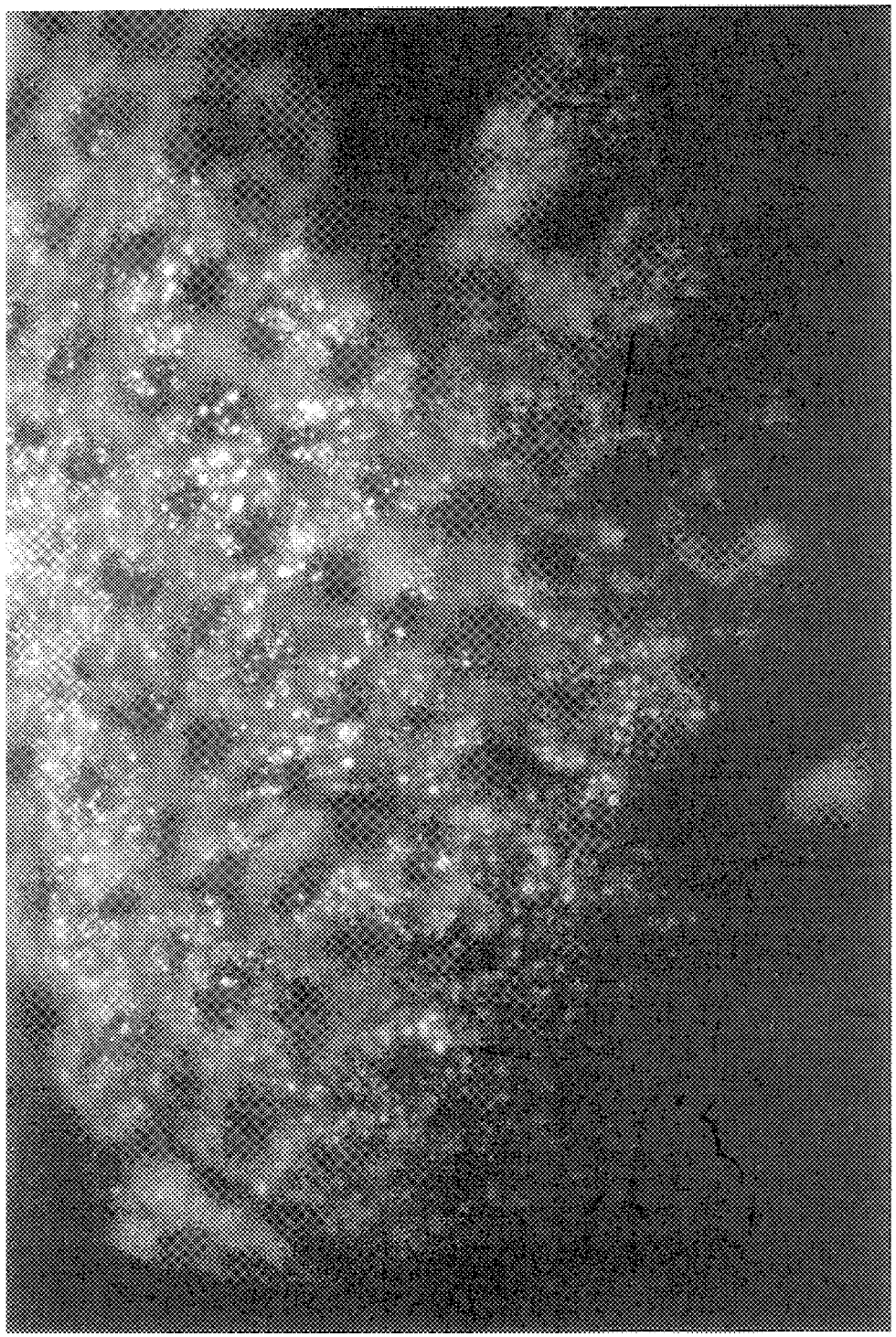

United States Patent
Te Koppele et al.

[11] Patent Number: 6,127,139
[45] Date of Patent: Oct. 3, 2000

[54] METHOD FOR ASSAYING PROTEOLYTIC ENZYMES USING FLUORESCENCE-QUENCHED SUBSTRATES

[75] Inventors: Johannes Maria Te Koppele, Leiderdorp; Bob Beekman, Leiden, both of Netherlands

[73] Assignee: Nederlands Organisatle voor Toegepast-Natuurwetenschappelijk Onderzoek (TNO), Delft, Netherlands

[21] Appl. No.: 09/101,167
[22] PCT Filed: Jan. 2, 1997
[86] PCT No.: PCT/NL97/00002
§ 371 Date: Jul. 2, 1998
§ 102(e) Date: Jul. 2, 1998
[87] PCT Pub. No.: WO97/25437
PCT Pub. Date: Jul. 17, 1997

[30] Foreign Application Priority Data

Jan. 4, 1996 [EP] European Pat. Off. ............ 96200017

[51] Int. Cl.[7] ............................. C12Q 1/37; C12Q 1/00; G01N 33/53
[52] U.S. Cl. ................................. 435/24; 435/23; 435/4; 435/968
[58] Field of Search ................................. 435/24, 23, 4, 435/968

[56] References Cited

FOREIGN PATENT DOCUMENTS

| | | |
|---|---|---|
| 0 428 000 | 5/1991 | European Pat. Off. . |
| 0 518 557 | 12/1992 | European Pat. Off. . |
| 2 278 356 | 11/1994 | United Kingdom . |
| WO 91/12338 | 8/1991 | WIPO . |
| WO 91/16336 | 10/1991 | WIPO . |
| WO 93/22429 | 11/1993 | WIPO . |

OTHER PUBLICATIONS

By H. Nagase, et al., Design and Characterization of a Fluorogenic Substrate Selectively Hydrolyzed by Stromelysin 1 (Matrix Metalloproteinase–3), *The Journal of Biological Chemistry*, vol. 269, No. 33, Aug. 19, 1994, pp. 20952–20957.

By G.M. McGeehan et al., "Characterization of the Peptide Substrate Specificities of Interstitial Collagenase and 92–kDa Gelatinase", *The Journal of Biological Chemistry*, vol. 269, No. 52, Dec. 30, 1994, pp. 32814–32820.

*Primary Examiner*—Louise N. Leary
*Attorney, Agent, or Firm*—Young & Thompson

[57] ABSTRACT

A method is disclosed for assaying a proteolytic enzyme comprising: (a) incubating an enzyme-containing sample with an immobilized fluorescence-quenched peptide having the formula Que-Sub-Flu-Spa-Car or Flu-Sub-Que-Spa-Car wherein Sub is a peptide chain containing a specific cleavage site for said proteolytic enzyme; Flu is a fluorophore; Que is a quencher capable of absorbing fluorescent radiation emitted by the fluorophore; Spa is a direct bond or a spacing chain; and Car is a water-insoluble and/or macromolecular carrier; (b) optionally separating the liquid from the carrier material; (c) irradiating said carrier material and measuring fluorescence. Also disclosed are immobilized substrates containing specific amino acid sequences for use in such an assay, especially in an assay for aggrecanase, and metalloproteinase-1, -3 and -13 activity.

19 Claims, 2 Drawing Sheets

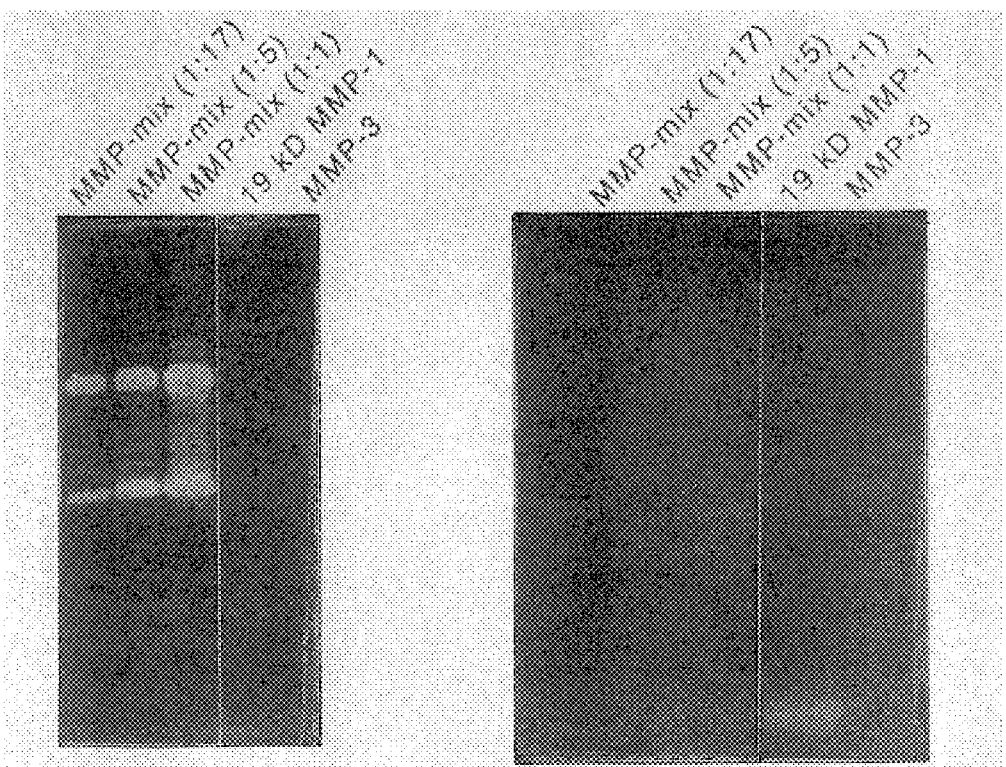

SEQUENCE LISTING

<160> NUMBER OF SEQ ID NOS: 43

<210> SEQ ID NO 1
<211> LENGTH: 10
<212> TYPE: PRT
<213> ORGANISM: Unknown
<220> FEATURE:
<223> OTHER INFORMATION: Description of Unknown Organism:UNKNOWN

<400> SEQUENCE: 1

-continued

Ile Thr Glu Gly Glu Ala Arg Gly Ser Val
 1               5                  10

<210> SEQ ID NO 2
<211> LENGTH: 10
<212> TYPE: PRT
<213> ORGANISM: Unknown
<220> FEATURE:
<223> OTHER INFORMATION: Description of Unknown Organism:UNKNOWN

<400> SEQUENCE: 2

Ile Thr Glu Gly Glu Ala Arg Gly Asn Val
 1               5                  10

<210> SEQ ID NO 3
<211> LENGTH: 10
<212> TYPE: PRT
<213> ORGANISM: Unknown
<220> FEATURE:
<223> OTHER INFORMATION: Description of Unknown Organism:UNKNOWN

<400> SEQUENCE: 3

Ala Ser Glu Leu Glu Gly Arg Gly Thr Ile
 1               5                  10

<210> SEQ ID NO 4
<211> LENGTH: 9
<212> TYPE: PRT
<213> ORGANISM: Unknown
<220> FEATURE:
<223> OTHER INFORMATION: Description of Unknown Organism:UNKNOWN

<400> SEQUENCE: 4

Phe Lys Glu Glu Glu Gly Leu Gly Ser
 1               5

<210> SEQ ID NO 5
<211> LENGTH: 9
<212> TYPE: PRT
<213> ORGANISM: Unknown
<220> FEATURE:
<223> OTHER INFORMATION: Description of Unknown Organism:UNKNOWN

<400> SEQUENCE: 5

Phe Arg Glu Glu Glu Gly Leu Gly Ser
 1               5

<210> SEQ ID NO 6
<211> LENGTH: 10
<212> TYPE: PRT
<213> ORGANISM: Unknown
<220> FEATURE:
<223> OTHER INFORMATION: Description of Unknown Organism:UNKNOWN

<400> SEQUENCE: 6

Pro Thr Ala Gln Glu Ala Gly Glu Gly Pro
 1               5                  10

<210> SEQ ID NO 7
<211> LENGTH: 10
<212> TYPE: PRT
<213> ORGANISM: Unknown
<220> FEATURE:
<223> OTHER INFORMATION: Description of Unknown Organism:UNKNOWN

<400> SEQUENCE: 7

Thr Ile Ser Gln Glu Leu Gly Gln Arg Pro
 1               5                  10

<210> SEQ ID NO 8
<211> LENGTH: 10
<212> TYPE: PRT
<213> ORGANISM: Unknown
<220> FEATURE:
<223> OTHER INFORMATION: Description of Unknown Organism:UNKNOWN

<400> SEQUENCE: 8

Thr Val Ser Gln Glu Leu Gly Gln Arg Pro
 1               5                  10

<210> SEQ ID NO 9
<211> LENGTH: 10
<212> TYPE: PRT
<213> ORGANISM: Unknown
<220> FEATURE:
<223> OTHER INFORMATION: Description of Unknown Organism:UNKNOWN

<400> SEQUENCE: 9

Thr Val Ser Gln Glu Leu Gly His Gly Pro
 1               5                  10

<210> SEQ ID NO 10
<211> LENGTH: 96
<212> TYPE: PRT
<213> ORGANISM: Unknown
<220> FEATURE:
<223> OTHER INFORMATION: Description of Unknown Organism:UNKNOWN

<400> SEQUENCE: 10

Val Lys Pro Ile Phe Glu Val Ser Pro Ser Pro Leu Glu Pro Glu Glu
 1               5                  10                  15

Pro Phe Thr Phe Ala Pro Glu Ile Gly Ala Thr Ala Phe Ala Glu Val
                20                  25                  30

Glu Asn Glu Thr Gly Glu Ala Thr Arg Pro Trp Gly Phe Pro Thr Pro
            35                  40                  45

Gly Leu Gly Pro Ala Thr Ala Phe Thr Ser Glu Asp Leu Val Val Gln
    50                  55                  60

Val Thr Ala Val Pro Gly Gln Pro His Leu Pro Gly Gly Val Val Phe
65                  70                  75                  80

His Tyr Arg Pro Gly Pro Thr Arg Tyr Ser Leu Thr Phe Glu Glu Ala
                85                  90                  95

<210> SEQ ID NO 11
<211> LENGTH: 14
<212> TYPE: PRT
<213> ORGANISM: Unknown
<220> FEATURE:
<223> OTHER INFORMATION: Description of Unknown Organism:UNKNOWN

<400> SEQUENCE: 11

Asp Phe Val Asp Ile Pro Asn Phe Phe Gly Val Gly Gly Glu
 1               5                  10

<210> SEQ ID NO 12
<211> LENGTH: 12
<212> TYPE: PRT
<213> ORGANISM: Unknown
<220> FEATURE:
<223> OTHER INFORMATION: Description of Unknown Organism:UNKNOWN

<400> SEQUENCE: 12

Ile Thr Glu Gly Gly Ala Arg Gly Ser Glu Ile Lys
 1               5                  10

<210> SEQ ID NO 13
<211> LENGTH: 12
<212> TYPE: PRT
<213> ORGANISM: Unknown
<220> FEATURE:
<223> OTHER INFORMATION: Description of Unknown Organism:UNKNOWN

<400> SEQUENCE: 13

Arg Pro Lys Pro Val Glu Val Trp Arg Glu Gly Lys
 1               5                  10

<210> SEQ ID NO 14
<211> LENGTH: 9
<212> TYPE: PRT
<213> ORGANISM: Unknown
<220> FEATURE:
<223> OTHER INFORMATION: Description of Unknown Organism:UNKNOWN

<400> SEQUENCE: 14

Pro Ala Ala Met His Ala Glu Gly Lys
 1               5

<210> SEQ ID NO 15
<211> LENGTH: 12
<212> TYPE: PRT
<213> ORGANISM: Unknown
<220> FEATURE:
<223> OTHER INFORMATION: Description of Unknown Organism:UNKNOWN

<400> SEQUENCE: 15

Ile Thr Glu Gly Glu Ala Arg Gly Ser Glu Ile Lys
 1               5                  10

<210> SEQ ID NO 16
<211> LENGTH: 9
<212> TYPE: PRT
<213> ORGANISM: Unknown
<220> FEATURE:
<223> OTHER INFORMATION: Description of Unknown Organism:UNKNOWN

<400> SEQUENCE: 16

Pro Gln Gly Leu Phe Ala Glu Ala Lys
 1               5

<210> SEQ ID NO 17
<211> LENGTH: 8
<212> TYPE: PRT
<213> ORGANISM: Unknown
<220> FEATURE:
<223> OTHER INFORMATION: Description of Unknown Organism:UNKNOWN

<400> SEQUENCE: 17

Pro Gln Gly Leu Phe Gly Glu Lys
 1               5

<210> SEQ ID NO 18
<211> LENGTH: 7
<212> TYPE: PRT
<213> ORGANISM: Unknown
<220> FEATURE:
<223> OTHER INFORMATION: Description of Unknown Organism:UNKNOWN

<400> SEQUENCE: 18

```
Pro Gln Gly Leu Glu Ala Lys
  1               5

<210> SEQ ID NO 19
<211> LENGTH: 7
<212> TYPE: PRT
<213> ORGANISM: Unknown
<220> FEATURE:
<223> OTHER INFORMATION: Description of Unknown Organism:UNKNOWN

<400> SEQUENCE: 19

Pro Gln Gly Leu Glu Gly Lys
  1               5

<210> SEQ ID NO 20
<211> LENGTH: 10
<212> TYPE: PRT
<213> ORGANISM: Unknown
<220> FEATURE:
<223> OTHER INFORMATION: Description of Unknown Organism:UNKNOWN

<400> SEQUENCE: 20

Pro Gln Gly Ala Arg Gly Ser Glu Ile Lys
  1               5                  10

<210> SEQ ID NO 21
<211> LENGTH: 7
<212> TYPE: PRT
<213> ORGANISM: Unknown
<220> FEATURE:
<223> OTHER INFORMATION: Description of Unknown Organism:UNKNOWN

<400> SEQUENCE: 21

Pro Arg Gly Leu Glu Ala Lys
  1               5

<210> SEQ ID NO 22
<211> LENGTH: 4
<212> TYPE: PRT
<213> ORGANISM: Unknown
<220> FEATURE:
<223> OTHER INFORMATION: Description of Unknown Organism:UNKNOWN

<400> SEQUENCE: 22

Pro Gln Gly Leu
  1

<210> SEQ ID NO 23
<211> LENGTH: 4
<212> TYPE: PRT
<213> ORGANISM: Unknown
<220> FEATURE:
<223> OTHER INFORMATION: Description of Unknown Organism:UNKNOWN

<400> SEQUENCE: 23

Pro Leu Gly Leu
  1

<210> SEQ ID NO 24
<211> LENGTH: 5
<212> TYPE: PRT
<213> ORGANISM: Unknown
<220> FEATURE:
<223> OTHER INFORMATION: Description of Unknown Organism:UNKNOWN
<220> FEATURE:
<221> NAME/KEY: UNSURE
<222> LOCATION: (5)
<223> OTHER INFORMATION: Xaa is any amino acid.
```

<400> SEQUENCE: 24

Ile Glu Gly Arg Xaa
 1               5

<210> SEQ ID NO 25
<211> LENGTH: 4
<212> TYPE: PRT
<213> ORGANISM: Unknown
<220> FEATURE:
<223> OTHER INFORMATION: Description of Unknown Organism:UNKNOWN

<400> SEQUENCE: 25

Ala Arg Gly Ser
 1

<210> SEQ ID NO 26
<211> LENGTH: 4
<212> TYPE: PRT
<213> ORGANISM: Unknown
<220> FEATURE:
<223> OTHER INFORMATION: Description of Unknown Organism:UNKNOWN

<400> SEQUENCE: 26

Arg Gly Leu Glu
 1

<210> SEQ ID NO 27
<211> LENGTH: 7
<212> TYPE: PRT
<213> ORGANISM: Unknown
<220> FEATURE:
<223> OTHER INFORMATION: Description of Unknown Organism:UNKNOWN

<400> SEQUENCE: 27

Pro Arg Gly Leu Glu Ala Lys
 1               5

<210> SEQ ID NO 28
<211> LENGTH: 6
<212> TYPE: PRT
<213> ORGANISM: Unknown
<220> FEATURE:
<223> OTHER INFORMATION: Description of Unknown Organism:UNKNOWN

<400> SEQUENCE: 28

Pro Val Glu Val Trp Arg
 1               5

<210> SEQ ID NO 29
<211> LENGTH: 4
<212> TYPE: PRT
<213> ORGANISM: Unknown
<220> FEATURE:
<223> OTHER INFORMATION: Description of Unknown Organism:UNKNOWN

<400> SEQUENCE: 29

Ala Ala Met His
 1

<210> SEQ ID NO 30
<211> LENGTH: 4
<212> TYPE: PRT
<213> ORGANISM: Unknown
<220> FEATURE:
<223> OTHER INFORMATION: Description of Unknown Organism:UNKNOWN

```
<400> SEQUENCE: 30

Leu Gly Leu Trp
 1

<210> SEQ ID NO 31
<211> LENGTH: 4
<212> TYPE: PRT
<213> ORGANISM: Unknown
<220> FEATURE:
<223> OTHER INFORMATION: Description of Unknown Organism:UNKNOWN
<220> FEATURE:
<221> NAME/KEY: SITE
<222> LOCATION: (1)
<223> OTHER INFORMATION: Xaa in position 1 is Gly, Ala, Abu, Val, Nva,
      Leu, Glu or Gln
<220> FEATURE:
<221> NAME/KEY: SITE
<222> LOCATION: (3)
<223> OTHER INFORMATION: Xaa in position 3 is Gly, Ala, Abu, Val, Nva or
      Leu
<220> FEATURE:
<221> NAME/KEY: SITE
<222> LOCATION: (4)
<223> OTHER INFORMATION: Xaa in position 4 is Arg, Gly, Ala, Abu, Val,
      Nva or Leu

<400> SEQUENCE: 31

Xaa Glu Xaa Xaa
 1

<210> SEQ ID NO 32
<211> LENGTH: 4
<212> TYPE: PRT
<213> ORGANISM: Unknown
<220> FEATURE:
<223> OTHER INFORMATION: Description of Unknown Organism:UNKNOWN
<220> FEATURE:
<221> NAME/KEY: SITE
<222> LOCATION: (1)
<223> OTHER INFORMATION: Xaa in position 1 is Pro or Hyp
<220> FEATURE:
<221> NAME/KEY: SITE
<222> LOCATION: (4)
<223> OTHER INFORMATION: Xaa in position 4 is Phe, Tyr, Trp or Cha

<400> SEQUENCE: 32

Xaa Asn Phe Xaa
 1

<210> SEQ ID NO 33
<211> LENGTH: 4
<212> TYPE: PRT
<213> ORGANISM: Unknown
<220> FEATURE:
<223> OTHER INFORMATION: Description of Unknown Organism:UNKNOWN
<220> FEATURE:
<221> NAME/KEY: SITE
<222> LOCATION: (1)
<223> OTHER INFORMATION: Xaa in position 1 is Gly, Ala, Abu or Val
<220> FEATURE:
<221> NAME/KEY: SITE
<222> LOCATION: (3)
<223> OTHER INFORMATION: Xaa in position 3 is Gly or Ala
<220> FEATURE:
<221> NAME/KEY: SITE
<222> LOCATION: (4)
<223> OTHER INFORMATION: Xaa in position 4 is Ser, Thr, Ala, Abu or Hse

<400> SEQUENCE: 33

Xaa Arg Xaa Xaa
 1
```

<210> SEQ ID NO 34
<211> LENGTH: 4
<212> TYPE: PRT
<213> ORGANISM: Unknown
<220> FEATURE:
<223> OTHER INFORMATION: Description of Unknown Organism:UNKNOWN
<220> FEATURE:
<221> NAME/KEY: SITE
<222> LOCATION: (1)
<223> OTHER INFORMATION: Xaa in position 1 is Arg, Lys, Orn, His or Trp
<220> FEATURE:
<221> NAME/KEY: SITE
<222> LOCATION: (2)
<223> OTHER INFORMATION: Xaa in position 2 is Gly, Ala, Abu or Val
<220> FEATURE:
<221> NAME/KEY: SITE
<222> LOCATION: (3)
<223> OTHER INFORMATION: Xaa in position 3 is Ala, Abu, Val, Nva, Leu,
      Nle or Ile

<400> SEQUENCE: 34

Xaa Xaa Xaa Glu
 1

<210> SEQ ID NO 35
<211> LENGTH: 4
<212> TYPE: PRT
<213> ORGANISM: Unknown
<220> FEATURE:
<223> OTHER INFORMATION: Description of Unknown Organism:UNKNOWN

<400> SEQUENCE: 35

Gly Glu Ala Arg
 1

<210> SEQ ID NO 36
<211> LENGTH: 4
<212> TYPE: PRT
<213> ORGANISM: Unknown
<220> FEATURE:
<223> OTHER INFORMATION: Description of Unknown Organism:UNKNOWN

<400> SEQUENCE: 36

Leu Glu Gly Arg
 1

<210> SEQ ID NO 37
<211> LENGTH: 4
<212> TYPE: PRT
<213> ORGANISM: Unknown
<220> FEATURE:
<223> OTHER INFORMATION: Description of Unknown Organism:UNKNOWN

<400> SEQUENCE: 37

Glu Glu Gly Leu
 1

<210> SEQ ID NO 38
<211> LENGTH: 4
<212> TYPE: PRT
<213> ORGANISM: Unknown
<220> FEATURE:
<223> OTHER INFORMATION: Description of Unknown Organism:UNKNOWN

<400> SEQUENCE: 38

Gln Glu Ala Gly
 1

```
<210> SEQ ID NO 39
<211> LENGTH: 4
<212> TYPE: PRT
<213> ORGANISM: Unknown
<220> FEATURE:
<223> OTHER INFORMATION: Description of Unknown Organism:UNKNOWN

<400> SEQUENCE: 39

Gln Glu Leu Gly
  1

<210> SEQ ID NO 40
<211> LENGTH: 4
<212> TYPE: PRT
<213> ORGANISM: Unknown
<220> FEATURE:
<223> OTHER INFORMATION: Description of Unknown Organism:UNKNOWN
<220> FEATURE:
<221> NAME/KEY: SITE
<222> LOCATION: (1)
<223> OTHER INFORMATION: Xaa in position 1 is Pro or Hyp
<220> FEATURE:
<221> NAME/KEY: SITE
<222> LOCATION: (3)
<223> OTHER INFORMATION: Xaa in position 3 is Gly, Ala, Abu or Val

<400> SEQUENCE: 40

Xaa Arg Xaa Leu
  1

<210> SEQ ID NO 41
<211> LENGTH: 6
<212> TYPE: PRT
<213> ORGANISM: Unknown
<220> FEATURE:
<223> OTHER INFORMATION: Description of Unknown Organism:UNKNOWN
<220> FEATURE:
<221> NAME/KEY: SITE
<222> LOCATION: (1)
<223> OTHER INFORMATION: Xaa in position 1 is Glu, Gln, Ala, Ser or Thr
<220> FEATURE:
<221> NAME/KEY: SITE
<222> LOCATION: (2)
<223> OTHER INFORMATION: Xaa in position 2 is Gly, Ala, Abu, Val, Nva,
      Leu, Glu or Gln
<220> FEATURE:
<221> NAME/KEY: SITE
<222> LOCATION: (4)
<223> OTHER INFORMATION: Xaa in position 4 is Gly, Ala, Abu, Val, Nva or
      Leu
<220> FEATURE:
<221> NAME/KEY: SITE
<222> LOCATION: (5)
<223> OTHER INFORMATION: Xaa in position 5 is Arg, Gly, Ala, Abu, Val,
      Nva or Leu
<220> FEATURE:
<221> NAME/KEY: SITE
<222> LOCATION: (6)
<223> OTHER INFORMATION: Xaa in position 6 is Gly, Glu or Gln

<400> SEQUENCE: 41

Xaa Xaa Glu Xaa Xaa Xaa
  1               5

<210> SEQ ID NO 42
<211> LENGTH: 6
<212> TYPE: PRT
<213> ORGANISM: Unknown
<220> FEATURE:
<223> OTHER INFORMATION: Description of Unknown Organism:UNKNOWN
<220> FEATURE:
<221> NAME/KEY: SITE
<222> LOCATION: (1)
```

```
<223> OTHER INFORMATION: Xaa in position 1 is Ala, Abu, Val, Nva, Leu,
      Nle or Ile
<220> FEATURE:
<221> NAME/KEY: SITE
<222> LOCATION: (2)
<223> OTHER INFORMATION: Xaa in position 2 is Pro or Hyp
<220> FEATURE:
<221> NAME/KEY: SITE
<222> LOCATION: (5)
<223> OTHER INFORMATION: Xaa in position 5 is Phe, Tyr, Trp or Cha
<220> FEATURE:
<221> NAME/KEY: SITE
<222> LOCATION: (6)
<223> OTHER INFORMATION: Xaa in position 6 is Ala, Abu, Val, Nva, Ile,
      Leu or Gly

<400> SEQUENCE: 42

Xaa Xaa Asn Phe Xaa Xaa
 1               5

<210> SEQ ID NO 43
<211> LENGTH: 6
<212> TYPE: PRT
<213> ORGANISM: Unknown
<220> FEATURE:
<223> OTHER INFORMATION: Description of Unknown Organism:UNKNOWN
<220> FEATURE:
<221> NAME/KEY: SITE
<222> LOCATION: (1)
<223> OTHER INFORMATION: Xaa in position 1 is Pro or Hyp
<220> FEATURE:
<221> NAME/KEY: SITE
<222> LOCATION: (2)
<223> OTHER INFORMATION: Xaa in position 2 is Arg, Lys, Orn, His or Trp
<220> FEATURE:
<221> NAME/KEY: SITE
<222> LOCATION: (3)
<223> OTHER INFORMATION: Xaa in position 3 is Gly, Ala, Abu or Val
<220> FEATURE:
<221> NAME/KEY: SITE
<222> LOCATION: (4)
<223> OTHER INFORMATION: Xaa in position 4 is a direct bond or Gly, Ala,
      Abu, Val, Nva, Leu, Nle or Ile
<220> FEATURE:
<221> NAME/KEY: SITE
<222> LOCATION: (5)
<223> OTHER INFORMATION: Xaa in position 5 is an amino acid capable of
      coupling to an amino group.
<220> FEATURE:
<221> NAME/KEY: SITE
<222> LOCATION: (6)
<223> OTHER INFORMATION: Xaa in position 6 is Gly, Ala, Abu, Val, Nva,
      Leu, Nle or Ile

<400> SEQUENCE: 43

Xaa Xaa Xaa Xaa Xaa Xaa
 1               5
```

METHOD FOR ASSAYING PROTEOLYTIC ENZYMES USING FLUORESCENCE-QUENCHED SUBSTRATES

The invention relates to a method for assaying a proteolytic enzyme comprising the use of a substrate having a fluorescent label and a fluorescence quencher.

Fluorometric assays for proteolytic enzymes, wherein a peptide substrate which is specifically cleaved by the enzyme and which carries a fluorophore at one side and a fluorescence quencher at the other side of the cleavage site are used, are known in the art. For example, EP-A-428000 discloses fluorescence-quenched substrates for detection of viral proteolytic enzymes, the substrates consisting of peptide sequences that can be specifically cleaved by the viral protease, to which are attached a fluorescent donor such as 5-(2-aminoethylamino)naphthalene-1-sulphonic acid (Edans), and a quencher, such as 4-(4-dimethylaminophenylazo)benzoic acid (Dabcyl). Upon contact with the specific proteolytic enzyme, the peptide is cleaved and the fluorescent donor is detached from the quenching acceptor, so that irradiation leads to a detectable fluorescence which is a measure for the specific enzymatic activity. A similar system for the detection of retroviral proteases is disclosed in EP-A-435845. Fluorogenic substrates that can be selectively hydrolysed by matrix metalloproteinase-3 (MMP-3) and to which a substituted coumarin and 2,4-dinitrophenyl are bound as a fluorophore and a quencher respectively, are described by Nagase et al., J. Biol. Chem. 269, 20952–20957 (1994). A general method for the preparation of such internally quenched fluorogenic protease substrates with the Edans/Dabcyl system, is described by Maggiora et al., J. Med. Chem. 35, 3727–3730 (1992).

Although these known substrates and methods allow proteolytic enzymes to be assayed with reasonable accuracy, known substrates and methods with fluorogenic proteinase substrates have been applied with purified enzymes and hardly with complex biological media (e.g. cell culture media, synovial fluid and other tissue fluids). These substrates and methods are likely to be subject to disturbances by fluorescent or light-absorbing constituents of more complex solutions than purified enzymes. According to the invention, a method is provided for quantitatively assaying proteolytic enzymes, using immobilised fluorescence-quenched substrates.

With the immobilized fluorescence-quenched substrates, e.g. on microtiter plates, the fluorescent fragments remain attached to the insoluble carrier after proteolytic cleavage. Thus, disturbing components of the reaction mixture (e.g. blood) can easily be washed away, providing a clean solution for use in the actual measurement. As a result, a more sensitive and reliable assessment of proteolytic enzyme activity is achieved.

Small peptide substrates for proteolytic enzymes suffer from the disadvantage that they may still be hydrolysed by high molecular weight complexes of proteinase and inhibitor, as is the case with matrix metalloproteinases inhibited by α2-macroglobulin (α2MG). Inasmuch as MMP-α2MG complexes are unable to hydrolyse the high molecular-weight physiological substrates such as proteoglycans, plasma proteins and collagen proteins, soluble peptide substrates overestimate the actual proteolytic activity. Immobilised fluorescence-quenched proteinase substrates are not hampered by this disadvantage: as a result of their immobilization, they are not converted any more by MMP-α2MG complexes. In this event, and all events mentioned below, immobilized is not limited to an insoluble carrier. Also, soluble carriers such as albumin, and macromolecules derived by any means, are applicable. In this context, macromolecules are understood as having a molecular weight of more than 5 kDa, especially more than 10 kDa.

Another aspect of the immobilization procedure is that the carrier (microtiter plate, paper or other strip) can be dried before performing the assay. This offers the advantage that reproducible and convenient assay kits can be developed which require minimal effort of the testing person. More importantly, the "dry format assay" allows assessment of proteolytic activity without dilution of the sample: it can be applied directly to the carrier. Thus, dilution of biological samples with proteolytic enzymes containing reversible, synthetic inhibitors is avoided. This is an advantage since dilution of such samples is likely to disturb the equilibrium of proteolytic enzyme and inhibitor with the consequence that artefactual data are obtained.

Immobilization of fluorescence-quenched substrates offers additional new possibilities to assess enzyme activity of proteinases.

1) When immobilised in acrylate gel, zymography-type of assays (see Hanemaaijer et al. Biochem. J. (1993) 296, 803–809) can be performed: first the proteolytic enzymes and their pro-forms are separated on the basis of their molecular weight. After electrophoresis components like sodium dodecyl sulphate have been washed off, proteinases and proforms renaturate and become active. With immobilized fluorescence-quenched substrates, an increase in fluorescence is observed. Advantages over conventional zymography are: peptides represent more general substrates (e.g. within one gel, several MMP's and proforms can be detected, in contrast to conventional zymography, where the included substrate gelatin, casein or other makes the assay more or less specific for one (group of) enzymes; selectivity towards specific proteinases can be achieved by selection of the proper peptide sequence. As such, synthetic peptides allow a far greater range of substrates to be used than physiological substrates: limited sources of, for instance collagen, are available. Furthermore, the use of immobilized fluorescence-quenched substrates allows continuous monitoring of fluorescence (in contrast to the "end point" conventional zymography method). Thus, low levels of proteinases can be detected in the presence of excessive amounts of other proteinases by determination of fluorescence at late and early points in time, respectively. Fluorescence-quenched zymography is a very sensitive technique, since fluorescence can be sensitively measured. In addition, it is a quantitative method, and it measures by an increase of a signal rather than a decrease in a signal as is the case with conventional zymography.

2) Immobilized fluorescence-quenched peptides may be applied in cell culture systems: growing cells on culture plates coated with fluorescence-quenched peptides allows assessment of production of proteolytic enzymes by the cultured cells. The peptides may also be physically (non-covalently) bound for studying cell migration.

3) Fluorescence-quenched peptides may be applied with tissue sections by bringing tissue in contact with a fluorescence-quenched substrate: fluorescence microscopy allows measurement of proteolytic enzyme activity at cellular level. This application can be performed with dissolved substrate, preferably in viscous medium such as polyvinyl alcohol or agarose to reduce diffusion of fluorescent products. Most ideally, the substrate is covalently bound to a macromolecule used to coat the histological support, or covalently bound to the support directly.

Proteinases are known to participate in tissue remodelling during physiological and pathological processes, through enzymatic digestion of various components of the extracellular matrix. Variation of active proteolytic enzymes may regulate the local accumulation or resorption of extracellular matrix, for instance in atherosclerosis, cartilage and bone turnover, and wound healing. Detection of proteolytic enzymes by immunohistology allows assessment of local amounts of proteinases. However, available antibodies do not distinguish between the pro-form, the active form, and the inhibited form of the enzyme. It would be more appropriate to have a methodology to assess the local enzyme activity of proteolytic enzymes rather than use the known immunological detection techniques. Such activity assay has been described recently by Galis et al. (FASEB J., 9 (1995) 974–980) with in situ zymography. Like SDS-PAGE format zymography, this represents an "end point" assay. Immobilized fluorescence-quenched substrates are perfectly suitable for use in microscopic localisation of active proteinases, because such use (1) allows local measurements, (2) allows measurements in time, (3) represents a quantitative method, (4) measures increase in signal rather than decrease in signal, (5) allows tissue section to be removed with continued monitoring of fluorescence (the tissue section has made an imprint), (6) is relatively easy to perform, (7) is applicable with virtually any buffer. With respect to items 2, 4, 5, 6 and 7, immobilised fluorescence-quenched substrates are superior over in situ zymography format as described by Galis et al.

The method according to the invention comprises:
(a) incubating an enzyme-containing sample with an immobilized fluorogenic peptide having the formula Que-Sub-Flu-Spa-Car or Flu-Sub-Que-Spa-Car wherein
Sub is a peptide chain containing a specific cleavage site for said proteolytic enzyme;
Flu is a fluorophore;
Que is a quencher capable of absorbing fluorescent radiation emitted by the fluorophore, which may also be the same groups as Flu;
Spa is a direct bond or a spacing chain; and
Car is an insoluble and/or macromolecular carrier;

(b) optionally separating the liquid from the carrier material;

(c) irradiating said carrier material and measuring fluorescence.

Apart from the symbols Flu, Sub, Que, Spa and Car defined above, the following abbreviations are used in this specification:

| Aad | α-aminoadipic acid |
| Abu | α-aminobutyric acid |
| Cha | β-cyclohexylalanine |

-continued

| Dabcyl | 4-(4-dimethylaminophenylazo)benzoic acid |
| DMF | dimethylformamide |
| DMSO | dimethylsulphoxide |
| DNP | dinitrophenyl |
| Eaca | ε-aminocaproic acid |
| Edans | 5-(2-aminoethylamino)naphthalene-1-sulphonic acid |
| EDTA | ethylenediaminetetraacetic acid |
| EGS | ethyleneglycol-bis(succinimidyl succinate) |
| Emc | S-mercaptoethylcysteine |
| Fmoc | 9-fluorenylmethoxycarbonyl |
| Gaba | γ-aminobutyric acid |
| HPLC | high performance liquid chromatography |
| Hse | homoserine (α-amino-γ-hydroxybutyric acid) |
| Hyp | 4-hydroxyproline |
| Mca | 7-methoxycoumarin-4-acetic acid |
| Mcc | 7-methoxycoumarin-3-carboxylic acid |
| MMP | matrix metalloproteinase |
| Nma | N-methylanthranilic acid |
| NMM | N-methylmorpholine |
| NMP | N-methylpyrrolidone |
| Nle | norleucine (α-aminocaproic acid) |
| Nva | norvaline (α-aminovaleric acid) |
| Orn | ornithine (α,δ-diaminovaleric acid) |
| PA | plasminogen activator |
| PAGE | polyacrylamide gel electrophoresis |
| PBS | phosphate buffered saline |
| SDS | sodium dodecyl sulphate |
| Sec | S-ethylcysteine (α-amino-β-ethylthio-propionic acid) |
| Smc | S-methylcysteine (α-amino-β-methylthio-propionic acid) |
| TFA | trifluoroacetic acid |
| Tris | tris(hydroxymethyl)aminomethane |

In the method according to the invention, the peptide chain Sub is selected in accordance with the specific proteolytic enzyme activity under assay. Proteolytic enzymes currently known can be divided in serine proteases (EC number 3.4.21), cysteine proteases (EC 3.4.22), aspartic proteases (EC 3.4.23), and metalloproteases (EC 3.4.24). For example, for the matrix metalloproteinases (MMP) the cleavage site is Gly-Leu and the amino acid sequence to be recognised by the MMP enzyme may be Pro-Xax-Gly-Leu, wherein Xax is any amino acid, in particular Pro-Gln-Gly-Leu (SEQ ID NO:22) or Pro-Leu-Gly-Leu (SEQ ID NO:23). As another example, plasmin specifically cleaves at the carboxyl function of lysine, and the specific sequence may e.g. be Ile-Phe-Lys-Xay. These and other specific protease substrate sequences are known in the art. Clinically important proteases comprise the following: factor VIIa, factor IXa, factor Xa, APC, thrombin, t-PA, u-PA, plasmin, trypsin, chymotrypsin, enterokinase, pepsin, cathepsins, angiotensin converting enzyme, matrix metalloproteinases (collagenases, stromelysins, gelatinases), elastase, Cir and Cis.

Some proteases with the relevant substrate specificity are as follows:

Cathepsin C: Cysteine protease catalysing the successive removal of N-terminal dipeptides form polypeptides. The reaction rate is dependent on the penultimate amino acid, whereby hydrophilic and hydrophobic residues are accepted. Degradation is blocked by N-terminal Lys or Arg. Pro as the second or third amino acid also prevents cleavage.

Chymotrypsin: Serine endopeptidase specifically hydrolysing peptide bonds at the C-termini of Tyr, Phe and Trp. Leu, Ala, Asp and Glu are cleaved at lower rates. Acts also upon amides and esters of susceptible amino acids.

Elastase: Serine endopeptidase, hydrolysing peptide bonds at the C-terminal side of amino acids with uncharged non-aromatic side chains like Ala, Val, Leu, Gly and Ser.

Factor Xa: Serine endopeptidase, hydrolysing specifically peptide bonds at the carboxylic side of Arg within the sequence -Ile-Glu-Gly-Arg-Xaz (SEQ ID NO:24) (Xaz is any amino acid).

Kallikrein: Serine endopeptidase, preferentially hydrolysing peptide and ester bonds at the carboxylic side of Arg, especially at Phe-(or Leu-)-Arg-Xaz bonds.

Pepsin: Aspartic endopeptidase with broad specificity. Cleaves preferentially bonds at the carboxylic side of Phe, Met, Leu or Trp which is bound to another hydrophobic residue. Tyr-Xaz bonds are relatively resistant.

Plasmin: Serine endopeptidase hydrolysing peptide and ester bonds at the carboxylic side of Lys or Arg.

Subtilisin: Unspecific serine endopeptidase that cleaves most peptide bonds, especially those adjacent to Asp, Glu, Ala, Gly and Val.

Thermolysin: Unspecific Zn-metallopeptidase that hydrolyses peptide bonds involving the amino group of hydrophobic amino acids with bulky side chains like Ile, Leu, Met, Phe, Trp and Val. The presence of Pro at the C-terminus of a hydrophobic amino acid prevents cleavage at the N-terminus of the latter.

Thrombin: Serine endopeptidase, hydrolysing specifically proteins and peptides at the carboxylic side of the basic amino acids Arg and Lys. Amide and ester bonds of Arg and Lys are cleaved as well.

Trypsin: Serine endopeptidase, hydrolysing specifically proteins and peptides at the carboxylic side of the basic amino acids Arg and Lys. Amide and ester bonds of Arg and Lys are also cleaved.

The method is suitable e.g. for assaying aggrecanase activity. Known aggrecanase cleavage sites (shown below with ▲) that can be used in such an assay include the following:

further sequence is preferably derived from the C-terminal region with respect to the cleavage site. An example is the human aggrecan sequence 382–477 as depicted in SEQ ID No: 10, which may contain one or more mutations.

The method is also suitable e.g. for assaying degradation of aggrecan by matrix metalloproteinases. The known MMP cleavage site (shown below with ▲) that can be used in such an assay includes the sequence:

$^{334}$Asp-Phe-Val-Asp-Ile-Pro-Asn▲Phe-Phe-Gly-Val-Gly-Gly-$^{348}$Glu (SEQ ID No: 11) (human aggrecan, cleavage by MMP-1, -2, -3, -7, -8, -9, and -13). In the sequence of the substrate, the underlined part should be present, conservative exchanges of $^{339}$Pro (e.g. by Hyp) and $^{342}$Phe (e.g. by Tyr, Trp of Cha) being allowed. Preferably, one more amino acid at either side, particularly two more and optionally three more amino acids at either of the underlined part is present. Here also, it may be advantageous to include a further partial sequence of e.g. 50–150 amino acids corresponding to the relevant aggrecan, which may be derived both from the N-terminal side and from the C-terminal side of the cleavage site.

The method is also suitable e.g. for assaying matrix metalloproteinase activity. Cleavage sites that can be used specifically e.g. for an MMP-13 assay include the sequence -Ala-Arg-Gly-Ser (SEQ ID NO:25), wherein Ala and Gly may be replaced by another aliphatic amino acid and Ser may be replaced by another hydroxy-aliphatic or aliphatic amino acid. Thus, a selective substrate for MMP-13 may be e.g. Dabcyl-Gaba-Ile-Thr-Glu-Gly-Gly-Ala-Arg▲Gly-Ser-Glu(Edans)-Ile-Lys-NH$_2$) (SEQ ID No: 12). Another cleavage site that can be used specifically for an MMP-13 assay includes the sequence Arg-Gly-Leu-Glu, wherein Arg may

| | |
|---|---|
| $^{369}$Ile-Thr-Glu-<u>Gly-Glu</u>▲<u>Ala-Arg</u>-Gly-Ser-$^{378}$Val | human and bovine aggrecan |
| $^{369}$Ile-Thr-Glu-<u>Gly-Glu</u>▲<u>Ala-Arg</u>-Gly-Asn-$^{378}$Val | rat aggrecan |
| $^{1541}$Ala-Ser-Glu-<u>Leu-Glu</u>▲<u>Gly-Arg</u>-Gly-Thr-$^{1550}$Ile | human aggrecan; similar sequence in rat aggrecan (residues 1270–1279) |
| $^{1710}$Phe-Lys-Glu-<u>Glu-Glu</u>▲<u>Gly-Leu</u>-Gly-$^{1718}$Ser | human aggrecan; similar sequence in bovine aggrecan (residues 1459–1467) |
| $^{1455}$Phe-Arg-Glu-<u>Glu-Glu</u>▲<u>Gly-Leu</u>-Gly- $^{1718}$Ser | rat aggrecan |
| $^{1815}$Pro-Thr-Ala-<u>Gln-Glu</u>▲<u>Ala-Gly</u>-Glu-Gly-$^{1824}$Pro | human aggrecan; similar sequence in bovine aggrecan (residues 1564–1573) and rat aggrecan (residues 1560–1569) |
| $^{1915}$Thr-Ile-Ser-<u>Gln-Glu</u>▲<u>Leu-Gly</u>-Gln-Arg-$^{1924}$Pro | human aggrecan |
| $^{1664}$Thr-Val-Ser-<u>Gln-Glu</u>▲<u>Leu-Gly</u>-Gln-Arg-$^{1673}$Pro | bovine aggrecan |
| $^{1660}$Thr-Val-Ser-<u>Gln-Glu</u>▲<u>Leu-Gly</u>-His-Gly-$^{1669}$Pro | rat aggrecan |

These sequences have SEQ ID No's: 1–9, respectively.

In these sequences, the underlined part should be present, optionally with conserved mutations, e.g. Ala, Abu, Val, Nva or Leu for Gly; Ala, Abu, Val, Nva, Ile or Nle for Leu; Gly, Abu, Val, Nva, Leu, Ile or Nle for Ala; Gln/Glu, Asn/Asp or Aad for Glu or Gln; Lys, Orn, His or Trp for Arg. Preferably one more amino acid at either side, particularly two more and optionally three more amino acids at either side of the underlined part are present, also possibly with conserved mutations. It is often advantageous to include in the substrate a further partial sequence of e.g. 50–150 amino acids corresponding to the relevant aggrecan either in the sequence Sub or in Car or in Spa. For the aggrecans, such a be replaced by another positively charged amino acid, or analogue, and Gly and/or Leu may be replaced by another aliphatic amino acid. Thus, a selective substrate for MMP-13 may be e.g. Dabcyl-Gaba-Pro-Arg-Gly▲Leu-Glu (Edans)-Ala-Lys-NH$_2$ (SEQ ID NO:27).

Similarly, Dabcyl-Gaba-Arg-Pro-Lys-Pro-Val-Glu▲Nva-Trp-Arg-Glu-(Edans)-Gly-Lys-NH$_2$ (SEQ ID No: 13) may be used as a selective fluorescence-quenched substrate for stromelysin (MMP-3); the amino acid sequence thereof was found by of Nagase et al (Nagase H, Fields C G, Fields G B. J. Biol. Chem. 269 (1994) 20952–20957) to be highly selective for MMP-3. The subsequence (Pro)-Val-Glu-Nva- Trp-(Arg) SEQ ID NO:28 should be present, with possible conserved variations.

Also Dabcyl-Gaba-Pro-Cha-Abu▲Smc-His-Ala-Glu (Edans)-Gly-Lys-NH$_2$ (SEQ ID No: 14) may be used as a selective substrate for assaying enzyme activity of interstitial collagenase (MMP-1); the amino acid sequence Cha-Abu-Smc-His (SEQ ID NO:29) was found by McGeehan et al. (McGeehan G M, Bickett D M, Green M, Kassel D, Wiseman J S, Berman J., J. Biol. Chem. 269 (1994) 32814–32820) to form a superior substrate over the natural sequence -Leu-Gly-Leu-Trp (SEQ ID NO:30). Variations thereof, such as Leu for Cha; Gly or Ala for Abu; Leu, Sec or Emc for Smc; and Trp for His, are also useful.

The fluorophore (Flu) can be a substituted amino acid or another substituted group capable of being attached to a peptide sequence, such as a substituted mercapto-acid, wherein the side-chain of the amino acid or other group carries the fluorescent moiety. The substituted amino acid may be a lysine, ornithine or other α,ω-diamino acid, to which the fluorescent moiety is bonded at an amino group, or Glu, Asp or Aad, to which the fluorescent moiety is bound by means of the terminal carboxyl function, or cysteine or other thiol-containing amino acid binding the fluorescent moiety through the thiol function.

Instead of being attached at the side chain of the peptide chain, the fluorophore may be attached between two amino acids, and thus be positioned in the peptide chain. In this embodiment, the fluorophore may contain e.g. an amino, mercapto, or hydroxy function at one end, and a carboxy function at the other end.

Fluorophores to be used in the substrates are known in the art. Suitable fluorophores comprise Edans described above and other aminonaphthalenesulphonic acids, coumarin, substituted coumarins such as 7-methoxycoumarin-4-acetic acid (Mca) or 7-methoxycoumarin-3-carboxylic acid (Mcc), tryptophane, N-methylanthranilic acid (Nma). The fluorophores may have excitation wavelengths between e.g. 250 and 400 nm and emission wavelengths e.g. between 370 and 550 nm.

The quencher (Que) can be attached to the specific substrate sequence e.g. by means of its carboxyl function, optionally through one or more spacing amino acids such as ω-amino-alkanoic acids, in particular γ-aminobutyric acid (Gaba), ε-aminocaproic acid (Eaca), ornithine or lysine. If the quencher is placed between the fluorophore and the carrier (formula Flu-Sub-Que-Spa-Car), it may be attached at the side chain of an amino acid or in between two amino acids, as described above for Flu.

Quenchers to be used in the substrates are known in the art. Suitable quenchers include Dabcyl described above and other aminophenylazobenzoyl derivatives and dinitrophenyl (DNP) and derivatives. The quencher preferably has an absorption wavelength that corresponds to the emission wavelength of the fluorophore. Therefore the quencher and the fluorophore are matched. Examples of suitable combinations of fluorophore and quencher are Edans/Dabcyl, coumarin/DNP, tryptophane/DNP and Nma/DNP. Since quenching of fluorescence may also occur between two identical fluorophores, efficient quenching can also be achieved when Que=Flu. The fluorophore and the quencher should be placed at such a distance that intramolecular energy transfer between the two is possible. This requirement will usually be met when the amino acid chain between the fluorophore and the quencher comprises 4–10 amino acids, especially 5–8 amino acids, or when the spatial distance between the fluorophore and the quencher corresponds to such a chain distance.

The spacing chain Spa may be a direct bond, a chain of one or more atoms, or a peptide or other chain providing sufficient distance between the substrate peptide and the insoluble carrier. The spacing chain can e.g. comprise one or more ω-amino acids such as Eaca. At its terminus, the spacing chain contains a group capable of covalent or other (e.g. biotin/avidin) coupling to the insoluble carrier. Coupling with the carrier may be established through homo- or bifunctional crosslinking agents coupling with amino, thiol or carboxyl functions. Suitable crosslinking or coupling agents include glutaric dialdehyde and commercially available amino-, sulpho- or carbo-link reagents. Coupling can also be performed by acrylate derivatives which can be incorporated in a polyacrylate matrix.

Preferably, the spacing chain and the carrier are bound to the substrate chain at its carboxyl terminus. If it is necessary for the coupling group at the end of the spacing chain to be bound to an amino terminus of the spacing chain, the "polarity" of the amino acid chain can be inversed by the introduction of e.g. a lysine or other α,ω-diamino acid. For example, a suitable spacing chain consists of a lysine residue, to which at its ω-amino position a Eaca residue is bound, to which, in turn, an acryloyl group is bound.

The insoluble and/or macromolecular carrier Car can comprise any conventional solid support used in biochemical assays. These include microtiter plates, paper strips, synthetic polymer strips, beads, resins, acrylate matrices (e.g. gels), glass, for instance after coating, and proteins.

The insoluble and/or macromolecular carrier Car can also comprise a macromolecular, dispersed or soluble, structure for use of the substrate as a model for natural enzyme substrates. This is especially useful when measuring enzyme activity depending on inhibitors and the like: a relatively small synthetic substrate not having a macromolecular carrier could be cleaved despite the presence of an inhibiting complex and thus measure an activity that would not be available for a "natural" macromolecular substrate.

The sequence Que-Sub-Flu-Spa-Car described above is often preferred over the sequence Flu-Sub-Que-Spa-Car, except when used as a macromolecular, dispersed or soluble substrate as describe above.

In a typical arrangement, a plurality of groups Flu-Sub-Que-Spa- is attached to a single carrier, resulting in the formula (Flu-Sub-Que-Spa)$_n$-Car. In exceptional cases where a gigh desnity of fluorophores is present (e.g. when n≧20, e.g. between 50 and 100), efficient quenching may be achieved without Que groups.

The method of the invention allows enzyme assays in various embodiments: 1) determination of enzyme activities in zymography format (substrate immobilized in/on acrylate gel); 2) enzyme measurement in microtiter plates and on or in other solid supports, allowing undiluted biological samples to be assayed and disturbing constituents of the biological matrix to be easily washed out; 3) assessment of proteolytic enzyme activity in tissue sections (histology); 4) enzyme measurement in solution or dispersion to mimic natural macromolecular substrates.

The proteolytic enzymes to be assayed using the method of the invention comprise all proteases including serine proteinases, cysteine proteinases, aspartic proteinases and metalloproteinases. The method is particularly useful with endoproteinases. A preferred class of proteinases to be assayed with the present method comprises the matrix metalloproteinases (MMP's) including collagenases, gelatinases and stromelysins. The MMP's play a role in wound healing, rheumatoid arthritis and osteoarthritis, tumor invasion and angiogenesis, through cell migration, cartilage degradation and basal membrane degradation and metastasis, respectively, and thus the activity of these enzymes is an important indicator for these conditions. An important advantage of the present method is that not only the active enzymes (MMP's) are detectable, but also the pro-enzymes, if the substrate is immobilised on or in acrylamide gel in zymography format.

The method of the invention can further be improved by selective removal, prior to the assay of the proteinase under investigation, of other proteolytic enzymes, e.g. using specific antibodies or other selective binding agents, by selective binding of the proteinase under investigation (with antibodies or other selective binding techniques) followed by separation of the unbound enzymes, or by addition of selective inhibitors of other proteolytic enzymes, or by addition of a selective inhibitor of the proteinase under investigation; in this latter case, the final result is obtained by substraction of the activity measured after inhibition from the total activity measured. All such assays include measurements of enzyme activities without sample pretreatment, or with any form of pretreatment of the biological sample including activation of pro-enzymes.

EXAMPLES

Example 1

Synthesis of Fluorogenic Peptides
Synthesis of Fmoc-Glu(Edans)—OH

To a stirred solution of Fmoc-Glu(OH)—O-tert-butyl (1.7 g, 4 mmol), Edans (1.07 g, 4 mmol) and benzotriazole-1-yloxy-tris(dimethylamino)-phosphonium hexafluorophosphate (1.77 g, 4 mmol) in 10 ml DMF was added at room temperature to di-iso-propylethylamine (2 ml, 12 mmol, destilled from $CaH_2$). After 2 h the reaction was complete (silica thin layer chromatography with toluene/acetic acid, 9/1, v/v). To the reaction mixture was added 50 ml $CH_2C_2$ and 50 ml 0.5 M $KHSO_4$. The organic layer was washed with 0.1 M $KHSO_4$ and $H_2O$, dried on $MgSO_4$, and evaporated in vacuo to yield 2.8 g of oil. To remove the tert-butyl group, 10 ml glacial acetic acid and 1 ml 12 N HCl were added. After stirring for 1 h, the solvents were evaporated in vacuo. Traces of acetic acid were removed by co-evaporation with DMF (2×10 ml). The product was purified by reverse-phase HPLC (RP-HPLC) in 45% yield (C18 column using a acetonitrile gradient in 0.1% TFA in $H_2O$).

Synthesis of Fluorescence-quenched Dabcyl/Edans Peptides

Substrates were synthesised at 10 µmol scale by solid phase chemistry on an automated multiple synthesiser using tentagelS AC (loading 0.2 µeq, particle size 90 µm). Repetitive couplings were performed by adding a mixture of 90 µl 0.67 M PyBOP (benzotriazole-1-yl-oxy-tris-pyrrolidino-phosphonium hexafluorophosphate) in NMP, 20 µl NMM (N-methylmorpholine) in NMP (2/1, v/v) and 100 µl of an 0.6 M solution of the appropiate Fmoc-amino acid in NMP. Coupling of Fmoc-Glu(Edans)—OH was performed with a 10-fold excess for 3 h. The Dabcyl moiety was coupled with a suspension of 10 equivalents p-(p-dimethylaminophenylazo)benzoic acid, 10 equivalents PyBOP and 20 equivalents NMM in 250 µl NMP for 3 h. Cleavage from the resin and removal of the protecting groups was performed by adding 200 µl $TFA/H_2O$ (19/1, v/v) to the reaction vessel (6 times at 5 min intervals). Three hours after the first $TFA/H_2O$ addition, the peptides were precipitated from the combined filtrates by addition of 10 ml ether/pentane (1/1, v/v) and cooling to −20° C., after which the peptides were isolated by centrifugation (−20° C., 2,500 g, 10 min.).

Subsequently, peptides were purified by RP-HPLC with a SuperPac Pep-S 15 µm 9.3×250 mm column. Purity and identity of the peptides was established by RP-HPLC (acetonitrile gradient in 0.1% TFA in $H_2O$) and by TOF-MALDI mass spectrometry.

Thus, fluorescence-quenched Dabcyl-Gaba-Ile-Thr-Glu-Gly-Glu▲Ala-Arg-Gly-Ser-Glu(Edans)-Ile-Lys-$NH_2$ (SEQ ID No: 15) was synthesised as a fluorescence-quenched substrate for aggrecanase, to be coupled to a carrier protein of about 100 amino acids, and Dabcyl-Gaba-Pro-Gln-Gly▲R as substrates for MMPs (examples of R: -Leu-Phe-Ala-Glu(Edans)-Ala-Lys-$NH_2$ (SEQ ID No: 16); -Leu-Phe-Gly-Glu-(Edans)-Lys-$NH_2$ (SEQ ID No: 17); -Leu-Glu(Edans)-Ala-Lys-$NH_2$ (SEQ ID No: 18); -Leu-Glu(Edans)-Gly-Lys-$NH_2$ (SEQ ID No: 19); -Leu-Glu(Edans)-Gly-$NH_2$ (SEQ ID No: 19 without terminal Lys); ▲, cleavage site). Moreover, R=Ala-Arg▲-Gly-Scr-Glu(Edans)-Ile-Lys-$NH_2$ (SEQ ID No: 20) was prepared as a selective substrate for MMP-13. In addition, Dabcyl-Gaba-Pro-Arg-Gly▲Leu-Glu(Edans)-Ala-Lys-$NH_2$ (SEQ ID No: 21) was synthesised as a selective substrate for MMP-13. In this latter sequence Leu may be replaced or even deleted.

Example 2

Immobilization of Fluorescence-quenched Peptides on Silica Beads

To 1.0 ml of fluorescence-quenched peptide solution (Dabcyl-Gaba-Pro-Gln-Gly▲R; 25 µM in phosphate buffered saline, R contains a lysine residue used for the immobilization), 10 mg of aminopropyl silica beads (40 µm diameter, 1.4 mmol amino groups per gram) was added. After 15 minutes of mixing at room temperature, 20 µl EGS solution (25 mM in DMSO) was added. The decline in A470 (absorbance maximum of Dabcyl) of the supernatant was used to monitor the reaction. Coupling was continued until A470 ceased to decrease. After centrifugation and removal of the supernatant, beads were washed successively with PBS (1.5 ml), PBS with 0.1% Tween-20 (1.5 ml), 1 M Tris HCl (pH 7.5; 1.2 ml), and incubation buffer (50 mM Tris, pH 7.6; 150 mM NaCl, 5 mM $CaCl_2$, 1 µM $ZnCl_2$, 0.01% Brij-35; 1.0 ml).

Upon incubation of peptide-labelled silica beads with a mixture of activated gelatinases (MMP-2 and MMP-9), the Dabcyl-Gaba-Pro-Gln-Gly fragment was effectively released from the beads into the supernatant, as verified by RP-HPLC (C18 column using a acetonitrile gradient in 0.1% TFA in $H_2O$).

Example 3

Immobilization of Fluorescence-quenched Peptides on Glass Slides

Glass microscope slides were thoroughly cleaned by washing in 20% $H_2SO_4$, water (two times), 0.1 N NaOH, and water. After drying, the glass slides were placed in 3-aminopropyltriethoxysilane for 4 minutes at room temperature, and rinsed with water and PBS (2 times). Under gentle agitation, glass slides were immersed in a solution of fluorescence-quenched substrate (e.g. Dabcyl-Gaba-Pro-Gln-Gly▲Leu-Phe-Ala-Glu(Edans)-Ala-Lys-$NH_2$ (SEQ ID No: 16) or Dabcyl-Gaba-Pro-Gln-Gly▲Leu-Glu(Edans)-Ala-Lys-$NH_2$ (SEQ ID No: 18); 25 µM in 1.0 ml PBS), to which 20 µl EGS (25 mM in DMSO) was added subsequently. Monitoring of A470 showed that coupling was complete within three hours at room temperature. Blocking of N-hydroxysuccinimidyl groups resulting from excess EGS was performed by addition of glycine in PBS (50 mM final concentration, 1.0 ml) for 1 hr. All steps were performed at ambient temperature.

Glass slides coated with fluorescence-quenched substrates were used to detect MMP activity in tissue sections as follows: cryostat sections (5 µm) of rabbit calvarial periost were placed on a substrate coated glass slide and incubated at 37° C. in a humid atmosphere in incubation buffer (50 mM Tris, pH 7.6, 5 mM $CaCl_2$, 1 µM $ZnCl_2$, 1 mM 4-aminophenylmercuric acetate). Appearance of fluorescence was followed with a fluorescence microscope. With time, increase in fluorescence was observed at the site of the tissue, as distinct fluorescent spots (FIG. 1). No fluorescence was detectable at sites of the glass not covered with tissue. Tissue sections incubated in the presence of EDTA or a synthetic MMP inhibitor showed substantially lower fluorescence. Furthermore, fluorescence of tissue sections not activated with 4-aminophenylmercuric acetate was lower than that of sections activated with 4-aminophenylmercuric acetate.

Example 4

Fluorescence-quenched Peptides Coupled to Bovine Serum Albumin

Fluorescence-quenched substrate (e.g. Dabcyl-Gaba-Pro-Gln-Gly▲Leu-Phe-Ala-Glu-(Edans)-Ala-Lys-$NH_2$ (SEQ ID No: 16); final concentration, 25 µM in PBS) was conjugated to bovine serum albumin (BSA; 2 mg/ml final concentration in PBS) by EGS (final concentration 0.5 mM; final volume, 2 ml) as described above. RP-HPLC analysis (linear gradient of acetonitrile in 0.1% TFA/$H_2O$) of incubations of the BSA-substrate with MMP-9 confirmed proteolysis of the protein-coupled substrate: after precipitation of protein, the Dabcyl-Gaba-Pro-Gln-Gly fragment was detected in the supernatant.

Example 5

Fluorescence-quenched MMP Substrate that is not Converted by α2-macroglobulin-complexed MMP Fluorescence-quenched substrate (e.g. Dabcyl-Gaba-Pro-Gln-Gly▲Leu-Phe-Ala-Glu(Edans)-Ala-Lys-$NH_2$ (SEQ ID No. 16); 1 mM DMSO, 200 µl) was derivatised with N-succinimidyl-S-acetylthioacetate (10 mM in DMSO, 50 µl), in the presence of triethylamine (100 mM in DMSO, 10 µl) for 30 minutes at room temperature. After de-acetylation of 80 nmol of the derivatised substrate (dissolved in 20 µl water, reacted with 25 µl sodium phosphate buffer, 50 mM, pH 7.5, comprising 25 mM EDTA and 0.5 M hydroxylamine, for 15 minutes at room temperature), 10 µl of maleimide activated ovalbumin (10 mg/ml; Pierce) was added. After 2 hours at room temperature, excess maleimide-ovalbumin was inactivated by addition of L-cystein (10 µl 20 mM in water). After dialysis (10 kDa cut off membrane) against water and incubation buffer (50 mM Tris, pH 7.6, 150 mM, NaCl, 5 mM $CaCl_2$, 1 µM $ZnCl_2$, 0.01% Brij-35), conversion of the ovalbumin-coupled substrate by MMP-13 (0.5 nM) was determined by the rate of increase of fluorescence (excitation, 360 nm; emission, 490 nm; fluorescence units per time).

In the presence of excess α2-macroglobulin (5 nM; pre-incubated with MMP-13 for 2 hours at 25° C.), less than 5% of the ovalbumin-coupled substrate was degraded compared to incubations lacking α2-macroglobulin. This indicates that assays with fluorescence-quenched substrates bound to a carrier do reflect inhibition of MMP activity by complexing with α2-macroglobulin.

Example 6

Incorporation of Fluorescence-quenched Peptides Into Polyacrylamide

Fluorescence-quenched substrate (e.g. Dabcyl-Gaba-Pro-Gln-Gly▲Leu-Phe-Ala-Glu-(Edans)-Ala-Lys-$NH_2$ (SEQ ID No: 16) and Dabcyl-Gaba-Pro-Gln-Gly▲Leu-Glu-(Edans)-Ala-Lys-$NH_2$ (SEQ ID No: 18); 25 nmol in 100 µl anhydrous DMSO) is derivatised into its acrylate derivative by addition of 75 nmol of N-(6-succinimidyloxy-6-oxyhexyl)-acrylamide or N-(4-succinimidyloxy-4-oxybutyl)-6-acrylamidohexanamide dissolved in anhydrous DMSO (5 mM), and 75 nmol of triethylamine (25 mM in anhydrous DMSO). The reaction was performed at room temperature and was complete after 3 hours (RP-HPLC).

Acrylate derivatives of fluorescence-quenched peptides were purified by RP-HPLC (acetonitrile gradient in 0.1% TFA/$H_2O$). After lyophilisation, 12.5 nmol of acrylate derivative was mixed with 3 ml (for 1 gel) of 10% acrylamide/bisacrylamide solution (75/2, v/v), followed by casting an SDS-PAGE gel according to standard procedures. Samples with matrix metalloproteinases or mixtures thereof, including inactive pro-forms were applied (20 µl) followed by conventional SDS-PAGE electrophoresis (8 mA per gel, 4° C., 4 hours). After electrophoresis, acrylamide gels were washed 3 times for 30 minutes in wash buffer (50 mM Tris, pH 7.6, 5 mM $CaCl_2$, 1 µM $ZnCl_2$, 2.5% Triton X-100) and two times for 10 minutes in incubation buffer (50 mM Tris, pH 7.6; 150 mM NaCl, 5 mM $CaCl_2$, 1 µM $ZnCl_2$, 0.01% Brij-35). After overnight incubation of the gel at 37° C. in incubation buffer, the gel was placed under UV-light (366 nm) and fluorescent bands at molecular weights corresponding to the matrix metalloproteinases and their pro-forms were observed (FIG. 2).

---

We claim:

1. A method for assaying a proteolytic enzyme comprising:
   (a) incubating an enzyme-containing sample with an immobilized fluorescence-quenched peptide having the formula Que-Sub-Flu-Spa-Car or Flu-Sub-Que-Spa-Car wherein
   Sub is a peptide chain containing a specific cleavage site for said proteolytic enzyme;
   Flu is a fluorophore;
   Que is a quencher capable of absorbing fluorescent radiation emitted by the fluorophore;
   Spa is a direct bond or a spacing chain; and
   Car is an water-insoluble and/or macromolecular carrier,
   (b) optionally separating the liquid from the carrier material;
   (c) irradiating said carrier material and measuring fluorescence.

2. The method according to claim 1, wherein Flu is an aminonaphthalenesulphonic acid group, and Que is an aminophenylazobenzoyl group.

3. The method according to claim 1, wherein Car is a polyacrylate or polyacrylamide.

4. The method according to claim 1, wherein Sub contains the amino acid sequence Xab-Glu-Xad-Xae (SEQ ID NO:31), wherein Xab is Gly, Ala, Abu, Val, Nva, Leu, Glu or Gln, Xad is Gly, Ala, Abu, Val, Nva or Leu, and Xae is Arg, Gly, Ala, Abu, Val, Nva or Leu, for assaying aggrecanase activity.

5. The method according to claim 1, wherein Sub contains the amino acid sequence Xai-Asn-Phe-Xaj (SEQ ID NO:32), wherein Xai is Pro or Hyp, and Xaj is Phe, Tyr, Trp or Cha, for assaying aggrecan degradation by matrix metalloproteinases.

6. The method according to claim 1 wherein Sub contains the amino acid sequence Xad-Arg-Xaf-Xag (SEQ ID NO:33), wherein Xad is Gly, Ala, Abu or Val, Xaf is Gly or Ala, and Xag is any amino acid, Ser, Thr, Ala, Abu or Hse, or the amino acid sequence Xam-Xan-Xao-Glu, (SEQ ID NO:34) wherein Xam is Arg, Lys, Orn, His or Trp, especially Arg, Xan is Gly, Ala, Abu or Val, Xao is Ala, Abu, Val, Nva, Leu, Nle or Ile, especially Leu, for assaying matrix metalloproteinase-13 activity.

7. The method according to claim 1 wherein said immobilized peptide is covalently or non-covalently bound to a solid support, such as a glass plate, for assaying proteinase activity in tissue sections.

8. An immobilized substrate for assaying a proteolytic enzyme, containing a fluorescence-quenched peptide having the formula Que-Sub-Flu-Spa-Car or Flu-Sub-Que-Spa-Car wherein Sub is a peptide chain containing a specific cleavage site for said proteolytic enzyme;

Flu is a fluorophore;

Que is a quencher capable of absorbing fluorescent radiation emitted by the fluorophore;

Spa is a direct bond or a spacing chain; and

Car is an insoluble and/or macromolecular carrier selected from a glass or polymer bead, a glass plate, a microtiter plate, a paper or synthetic polymer strip, an acrylate or acrylamide gel and a protein.

9. A labelled oligopeptide as a substrate for aggrecanase activity comprising one of the following sequences: Gly-Glu-Ala-Arg (SEQ ID NO:35), Leu-Glu-Gly-Arg (SEQ ID NO:36), Glu-Glu-Gly-Leu (SEQ ID NO:37), Gln-Glu-Ala-Gly (SEQ ID NO:38) and Gln-Glu-Leu-Gly (SEQ ID NO:39).

10. A labelled oligopeptide as a substrate for matrix metalloproteinase-13 activity, comprising the amino acid sequence Xad-Arg-Xaf-Leu (SEQ ID NO:40) wherein Xad is Pro or Hyp and Xaf is Gly, Ala, Abu or Val.

11. A labelled oligopeptide as a substrate for aggrecanase activity comprising the amino acid sequence Xab-Glu-Xad-Xae (SEQ ID NO:31), wherein Xab is Gly, Ala, Abu, Val, Nva, Leu, Glu or Gln, Xad is Gly, Ala, Abu, Val, Nva or Leu, and Xae is Arg, Gly, Ala, Abu, Val, Nva or Leu, to which a fluorescent label and preferably also a quenching group are bound.

12. The oligopeptide according to claim 11, comprising the amino acid sequence Xaa-Xab-Glu-Xad-Xae-Xaf (SEQ ID NO:41), wherein Xaa is Glu, Gln, Ala, Ser or Thr, and/or Xaf is Gly, Glu or Gln, and Xab, Xad and Xae are as defined in claim 11.

13. A labelled oligopeptide as a substrate for aggrecan degrading activity by matrix metalloproteinases comprising the amino acid sequence Xah-Xai-Asn-Phe-Xaj-Xak (SEQ ID NO:42), wherein Xah is Ala, Abu, Val, Nva, Leu, Nle or Ile, Xai is Pro or Hyp, Xaj is Phe, Tyr, Trp or Cha, and Xak is Ala, Abu, Val, Nva, Ile, Leu or Gly, to which a fluorescent label are bound.

14. A labelled oligopeptide as a substrate for matrix metalloproteinase-13 activity, comprising the amino acid sequence Xad-Arg-Xaf-Xag (SEQ ID NO:33), wherein Xad is Gly, Ala, Abu or Val, Xaf is Gly or Ala, and Xag is an aliphatic amino acid, to which a fluorescent label are bound.

15. A labelled oligopeptide as a substrate for matrix metalloproteinase-13 activity, comprising the amino acid sequence Xal-Xam-Xan-Xao-Xap-Xaq (SEQ ID NO:34), wherein Xal is Pro or Hyp, Xam is Arg, Lys, Orn, His or Trp, Xan is Gly, Ala, Abu or Val, Xao is a direct bond or Gly, Ala, Abu, Val, Nva, Leu, Nle or Ile, Xap is an amino acid capable of coupling to an amino group, and Xaq is Gly, Ala, Abu, Val, Nva, Leu, Nle or Ile, to which a fluorescent label are bound.

16. The oligopeptide according to claim 9, having a fluorescent label and a quenching group.

17. A labelled oligopeptide as a substrate for matrix metalloproteinase-1 (interstitial collagenase) activity, comprising the amino acid sequence Cha-Abu-Smc-His (SEQ ID No. 29) to which a fluorescent label and a quenching group are bound.

18. A labelled oligopeptide as a substrate for matrix metalloproteinase-3 (stromelysin) activity, comprising the amino acid sequence Val-Glu-Nva-Trp (SEQ ID No. 30), to which Edans as a fluorescent label and Dabcyl as a quenching group are bound.

19. The oligopeptide according to claim 9, bound to a water-insoluble carrier or to a protein.

* * * * *